United States Patent [19]
Weisz

[11] Patent Number: 5,935,940
[45] Date of Patent: Aug. 10, 1999

[54] COMPOSITIONS AND METHODS FOR MODULATING GROWTH OF A TISSUE IN A MAMMAL

[75] Inventor: Paul B. Weisz, State College, Pa.

[73] Assignee: Trustees of the University of Pennsylvania, Philadelphia, Pa.

[21] Appl. No.: 08/906,500

[22] Filed: Aug. 5, 1997

Related U.S. Application Data

[62] Division of application No. 08/345,011, Nov. 23, 1994, Pat. No. 5,658,894, which is a continuation of application No. 07/900,592, Jun. 18, 1992, abandoned, and a continuation-in-part of application No. 07/790,320, Nov. 12, 1991, abandoned, which is a continuation of application No. 07/691,168, Apr. 24, 1991, abandoned, which is a continuation of application No. 07/397,559, Aug. 23, 1989, abandoned, said application No. 07/900,592, is a continuation-in-part of application No. 07/480,407, Feb. 15, 1990, Pat. No. 5,183,809.

[51] Int. Cl.$^6$ .......................... A61K 31/715; A61K 38/00
[52] U.S. Cl. ............................. 514/58; 514/21; 530/810; 530/812; 530/813
[58] Field of Search ........................ 514/58, 21; 530/810, 530/812, 813

[56] References Cited

U.S. PATENT DOCUMENTS

| | | | |
|---|---|---|---|
| 2,923,704 | 5/1960 | Berger et al. | 514/58 |
| 3,420,788 | 1/1969 | Solms | 260/17.4 |
| 4,020,160 | 4/1977 | Bernstein et al. | 424/180 |
| 4,066,829 | 1/1978 | Nair et al. | 536/103 |
| 4,247,535 | 1/1981 | Lewis et al. | 424/180 |
| 4,258,180 | 3/1981 | Lewis et al. | 536/112 |
| 4,383,992 | 5/1983 | Lipari | 424/238 |
| 4,582,900 | 4/1986 | Brandt et al. | 536/103 |
| 4,596,795 | 6/1986 | Pitha | 514/58 |
| 4,727,064 | 2/1988 | Pitha | 514/58 |
| 4,764,604 | 8/1988 | Müller | 536/103 |
| 4,774,329 | 9/1988 | Friedman | 536/103 |
| 4,834,985 | 5/1989 | Elger et al. | 424/488 |
| 4,840,941 | 6/1989 | Ueno et al. | 514/59 |
| 4,869,904 | 9/1989 | Uekama et al. | 424/400 |
| 4,877,774 | 10/1989 | Pitha et al. | 514/26 |
| 4,877,778 | 10/1989 | Carpenter et al. | 514/58 |
| 4,902,788 | 2/1990 | Zemel et al. | 536/1.1 |
| 4,912,093 | 3/1990 | Michaeli | 514/53 |
| 4,929,577 | 5/1990 | Cornell | 514/58 |
| 4,949,602 | 8/1990 | Harker et al. | 514/18 |
| 5,019,562 | 5/1991 | Folkman et al. | 514/58 |
| 5,068,226 | 11/1991 | Weinshenker et al. | 514/58 |
| 5,075,432 | 12/1991 | Vanzo | 536/103 |
| 5,100,878 | 3/1992 | Geber | 514/58 |
| 5,135,919 | 8/1992 | Folkman et al. | 514/56 |
| 5,164,379 | 11/1992 | Koslo et al. | 514/58 |
| 5,183,809 | 2/1993 | Weisz et al. | 514/58 |
| 5,248,675 | 9/1993 | Kurita et al. | 514/58 |
| 5,441,944 | 8/1995 | Weisz et al. | 514/58 |
| 5,446,030 | 8/1995 | Weisz et al. | 514/58 |
| 5,516,766 | 5/1996 | Weisz et al. | 514/58 |
| 5,637,575 | 6/1997 | Herrmann et al. | 514/58 |
| 5,658,894 | 8/1997 | Weisz | 514/58 |
| 5,760,015 | 6/1998 | Joullié et al. | 514/58 |
| 5,776,914 | 7/1998 | Weisz et al. | 514/58 |

FOREIGN PATENT DOCUMENTS

| | | |
|---|---|---|
| 0 121 777 | 10/1984 | European Pat. Off. . |
| 0 188 821 | 7/1986 | European Pat. Off. . |
| 0 193 850 | 9/1986 | European Pat. Off. . |
| 0 325 199 | 7/1989 | European Pat. Off. . |
| 0 447 171 | 9/1991 | European Pat. Off. . |
| 3819498 A1 | 12/1988 | Germany . |
| 50-36422 | 4/1975 | Japan . |
| 50-140476 | 11/1975 | Japan . |
| 58-171404 | 10/1983 | Japan . |
| 62-123196 | 6/1987 | Japan . |
| 63-122701 | 5/1988 | Japan . |
| 1-315401 | 12/1989 | Japan . |
| WO 85/02767 | 7/1985 | WIPO . |
| WO 87/05808 | 10/1987 | WIPO . |
| WO-89/06536 | 7/1989 | WIPO . |

OTHER PUBLICATIONS

Skubitz et al. *Cell Mol. Biol.*, vol. 38(6):543–560, 1992.

Teicher et al. Cancer Chemotherapy and Pharmacology vol. 38(2): 169–177, 1996.

*Chemical Abstracts*, 1975, 83 : 79544a.

Folkman et al., 1977, *Science*, 235:442–447.

*Chemical Abstracts*, 1982, 96 :218351u.

*Chemical Abstracts,,* 1975, 83:79544a.

Leveen et al., 1982, *Investigative Radiology*, 17:470–475.

Uekama et al., 1982, *International Journal of Pharmaceutics*, 10: 1–15.

Croft et al., 1983 *Tetrahedron*, 39:1417–1474.

Fenyvesi et al., 1984, *Chem. Pharm. Bull.*, 32(2): 665–669.

Crum, "A New Class of Steroids Inhibits Angiogenesis in the Presence of Heparin or a Heparin Fragment," 1985, *Science*, 230:1490–1493.

Komiyama et al., 1986, *Polymer Journal*, 18(4): 375–377.

Pitha et al., 1986, *Journal of Pharmaceutical Sciences,:* 75(2):165–167.

Nakashima et al., 1987, *Antimicrobial Agents and Chemotherapy*, 1524–1528.

(List continued on next page.)

*Primary Examiner*—Howard C. Lee
*Attorney, Agent, or Firm*—Panitch Schwarze Jacobs & Nadel, P.C.

[57] ABSTRACT

Polyionic derivatives of cyclodextrins and methods for preparing these derivatives are provided in which a polyionic derivative of cyclodextrin is combined with a growth factor, preferably a heparin binding growth factor. These compositions are of low solubility and are applied directly to the location of a wound. By virtue of the low solubility, the compositions remain in place at the site of application and slowly release growth factor. In an alternative embodiment, the cyclodextrin derivatives are administered in the absence of growth factor and are used to absorb growth factor present in the body at the location of the wound in order to prevent overstimulation of the wound response.

29 Claims, 5 Drawing Sheets

OTHER PUBLICATIONS

Lobb, "Clinical Applications of Heparin–Binding Growth Factors", 1988, *European Journal of Clinical Investigation,* 18:321–328.

Pow et al., "Low Molecular Weight Heparin Reduces Restenosis After Experimental Angioplasty," 1989, *Circulation,* 88(4), Suppl. II.

Yamamoto et al., 1989, *International Journal of Pharmaceutics,* 49:163–171.

Antoniades et al., "Injury Induces In Vivo Expression of Platelet–Derived Growth Factor (PDGF) and PDGF Receptor mRNAs in Skin Epithelial Cells and PDGF mRNA in Connective Tissue Fibroblasts" 1991, *Proc. Natl. Acad. Sci. USA,* 88:565–569.

Herrmann, *Abstracts of Papers,* National Meeting of the American Heart Association, Anaheim, CA, Nov. 11–14, 1991.

Pierce et al., 1991, *J. Cell Biochem.,* 45:319–326.

n = 6, 7 or 8 n = 7

MW
94,000 
68,000 
43,000 
30,000 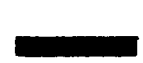  
21,000 
18,400   
14,300 
LANE    1   2   3
FIG. 4

COMPOSITIONS AND METHODS FOR MODULATING GROWTH OF A TISSUE IN A MAMMAL

CROSS REFERENCE TO RELATED APPLICATIONS

This is a division of application Ser. No. 08/345,011, filed Nov. 23, 1994 (U.S. Pat. No. 5,658,894, issued Aug. 19, 1997), which is a continuation of application Ser. No. 07/900,592, filed Jun. 18, 1992 (abandoned) and a continuation-in-part of application Ser. No. 07/790,320, filed Nov. 12, 1991 (abandoned), which is a continuation of application Ser. No. 07/691,168, filed Apr. 24, 1991 (abandoned), which is a continuation of Application Ser. No. 07/397,559, filed Aug. 23, 1989 (abandoned). Application Ser. No. 07/900,592 is a continuation-in-part of application Ser. No. 07/480,407, filed Feb. 15, 1990 (U.S. Pat. No. 5,183,809, issued Feb. 2, 1993). All of the aforesaid applications and issued patents are hereby incorporated by reference.

FIELD OF THE INVENTION

The present invention is directed to compounds, compositions and methods for healing wounded living tissue, and particularly to saccharide-based compounds and compositions which remain localized at the site of a wound for extended periods of time.

BACKGROUND OF THE INVENTION

The injury of tissue initiates a series of events that result in tissue repair and healing of the wound. During the first several days following an injury, there is directed migration of neutrophils, macrophages and fibroblasts to the site of the wound. The macrophages and fibroblasts which migrate to the wound site are activated, thereby resulting in endogenous growth factor production, synthesis of a provisional extracellular matrix, proliferation of fibroblasts and collagen synthesis. Finally from about two weeks to one year after infliction of the wound there is remodeling of the wound with active collagen turn over and cross linking (Pierce et al., 1991, J. Cell Biochem., 45:319–326). The manner in which this repair process is regulated is mostly unknown; it is known, however, that cell proliferation, migration and protein synthesis can be stimulated by growth factors that act on cells having receptors for these growth factors.

In vivo studies have shown that local application of exogenous single growth factors or a combination of growth factors can enhance the healing process following experimental wounding in animals (Antoniades et al., 1991, Proc. Natl. Acad. Sci. USA, 88:565–569). The ability of these growth factors to promote wound healing has resulted in efforts to obtain these factors in purified form. It is known that a number of these growth factors, known as heparin binding growth factors (HBGFs), have a strong affinity for heparin (reviewed in Lobb, 1988, Eur. J. Clin. Invest. 18:321–328 and Folkman and Klagsbrun, 1987, Science 235:442–447). Accordingly heparin affinity chromatography has been used to obtain these growth factors in purified form. In addition the DNA coding for a number of these growth factors has been isolated and the proteins can be produced by recombinant DNA methods. These HBGFs have been shown to have mitogenic and non-mitogenic effects on virtually all mesoderm and neuroectoderm derived cells in vitro. HBFGs are also known to promote the migration, proliferation and differentiation of these cells in vivo. It was suggested by Lobb (1988, Eur. J. Clin. Invest., 18:321–328) that HBGFs could therefore effect the repair of soft tissue. It was further suggested that HBGFs may be used to effect the repair of hard tissue such as bone and cartilage. In contrast to their beneficial effects, it is also known that growth factors may over-stimulate the wound healing response, resulting in the excessive smooth muscle cell proliferation and migration which occur, for example, in restenosis following angioplasty.

Knowledge of the affinity of growth factors for heparin and the difficulty of obtaining heparin in a pure, homogeneous form has resulted in attempts to obtain a compound which possesses heparin's affinity for growth factors but which could be easily and reproducibly manufactured. As described in the parent applications referenced hereinabove, one group of compounds meeting these requirements are cyclodextrins, cyclic oligosaccharides consisting of up to at least six glucopyranose units.

U.S. Pat, No. 5,019,562 to Folkman et al. (the Folkman et al. patent), which is in the lineage leading to the present application, is directed to the use of highly soluble cyclodextrin derivatives to treat undesirable cell or tissue growth. The cyclodextrin derivatives disclosed in this patent are combined with growth inhibiting steroids or administered alone to absorb growth factors present in the blood stream. The cyclodextrin derivatives disclosed in the Folkman et al. patent are highly hydrophilic and therefore highly soluble. The high solubility of these derivatives is said to be an important factor which cooperatively interacts with the inherent complexing ability of the cyclodextrin structure for exogenous steroids. In addition, the high solubility of these compounds is said to facilitate introduction of the compounds into the body and to aid in dispersal via the blood stream.

SUMMARY OF THE INVENTION

The high solubility of the compounds disclosed in the Folkman et al. patent is desirable for systemic administration of these compositions to the body; on the other hand, however, applicants have found that the high solubility of these compounds limits their ability to remain localized in the area of a wound following administration. To maximize delivery of a given growth factor or factors to a wound site, applicants have discovered that it is desirable to obtain saccharide-based compounds possessing a high affinity for growth factor and very low solubility. According to one aspect of applicants' discovery, such low solubility compounds are combined with a growth factor prior to administration to the body and applied locally to the site of a wound. Due, at least in part, to their low solubility, such compounds remain at the site of application and slowly release the growth factor to optimize the dosage of growth factor at the wound site. Applicants have also found that, alternatively, a compound possessing both a high affinity for growth factor and a low solubility can be used to remain at the site of an injury and to absorb at least some portion of the growth factors released by the injured tissue, thereby reducing the probability of over-stimulation of the wound healing process, as is observed in restenosis following angioplasty.

In view of both the beneficial and pathological properties of growth factors involved in wound repair, applicants have thus-identified a need for compositions which regulate the concentration and/or diffusion of growth factors in the area of a wound so as to optimize the wound healing process. Accordingly, the present invention provides low solubility polyanionic saccharide derivatives having a high negative charge density for affecting the growth of living tissue in mammals. Also provided are compositions comprising all active agent comprising low solubility polyanionic saccharide derivative and a physiologically acceptable carrier for the saccharide derivative.

The saccharide derivative preferably has a body temperature solubility of less than about 15 grams per 100 ml of water. According to certain preferred embodiments, the saccharide derivatives have substantially no solubility in water at body temperature. The term "body temperature" as used herein refers to the range of body temperatures expected for a living mammal, including the lowered body temperatures used in various surgical techniques and the elevated body temperatures encountered in physiological responses to infection. Unless otherwise indicated, solubility refers to solubility in distilled water.

The compositions of the present invention offer a number of advantages over prior art compositions due, at least in part, to the low solubility of the active ingredient in body tissues and fluid. The low solubility of the present saccharide derivatives is advantageous in wound healing methods which provide for administration directly to the site of a wound. The compositions remain substantially at the administered location for an extended period of time. When combined with growth factors, the saccharide derivatives of the present invention facilitate controlled release of the growth factors at the wound site, thereby regulating and greatly enhancing the wound healing process. In the absence of a growth factor, the present compositions can, by virtue of their affinity for growth factors, reduce the local concentration and/or diffusion of growth factors produced by cells at the wound site as well as growth factors present in the blood stream. By reducing the diffusion of growth factors, the compositions are capable of preventing or substantially reducing over-stimulation of the wound healing response, thereby avoiding the pathological growth of cells that results in such conditions as restenosis following angioplasty, vein graft intimal hyperplasia, and native vessel atherosclerosis.

The present invention also provides methods for the preparation of beneficial wound healing compositions. These compositions comprise relatively insoluble solid forms of highly anionic polysaccharides. The method aspects comprise reacting a saccharide with an anionic derivatizing agent to generate a polyanionic derivative of the saccharide, followed by salt formation of the largely insoluble product. Alternatively, saccharides are reacted with a suitable coupling agent to generate a sparsely soluble polymer or copolymer of that saccharide, followed by a reaction with an anionic derivatizing agent. According to certain embodiments, these derivatized saccharides are then combined with one or more growth factors. The compositions provided by these methods of preparation have the advantageous properties of very low solubility and high growth factor affinity.

The present invention also provides wound healing methods. According to these methods, the present low solubility, polyanionic saccharide derivatives are applied to the area to be treated. Such methods are adaptable for use in the prevention of restenosis, promotion of angiogenesis, treatment of transplanted tissue or organs and treatment of damaged or transplanted bone or cartilage.

The ability of the present compounds and compositions to regulate the wound healing process offers possible life-saving benefits to patients who have undergone procedures such as percutaneous transluminal angioplasty (hereinafter "PCTA"). It has been observed that up to 40% of patients who undergo PCTA are afflicted by restenosis and the recurrent arterial blockage that it causes. Thus, the long-term effectiveness of treatments for arteriosclerosis, such as angioplasty, have been substantially limited by the reoccurrence of restenosis. It is believed that the present compositions will substantially reduce or eliminate restenosis and thereby have a major influence on the morbidity and mortality rate for patients which have undergone angioplasty, vein graft bypass operations and similar procedures. In addition, it is expected that victims of cardiac, cerebral or peripheral ischemic disease will greatly benefit from use of the compositions of the present invention. In particular, patients who suffer from infarcted myocardial tissue require the establishment of new collateral blood capillaries and vessels to supply blood to the infarcted tissue. The present compositions may include growth factors to promote angiogenesis at the site of the infarcted tissue. These examples represent just a few of the possible life-saving benefits offered by the compositions and methods of the present invention.

BRIEF DESCRIPTION OF THE FIGURES

FIG. 4 shows polyacrylamide gel electrophoresis of basic fibroblast growth factor and chondrosarcoma derived growth factor purified by cyclodextrin copper biaffinity chromatography. Lane 1 shows the protein profile of the protein markers (phosphorylase b, bovine serum albumin, ovalbumin, carbonic anhydrase, soybean trypsin inhibitor, beta lactoglobulin, and lysozyme). Lanes 2 and 3 show the 18,000 molecular weight polypeptide bands of basic fibroblast growth factor and chondrosarcoma derived growth factor, respectively.

DETAILED DESCRIPTION OF THE INVENTION

Figure 1A:
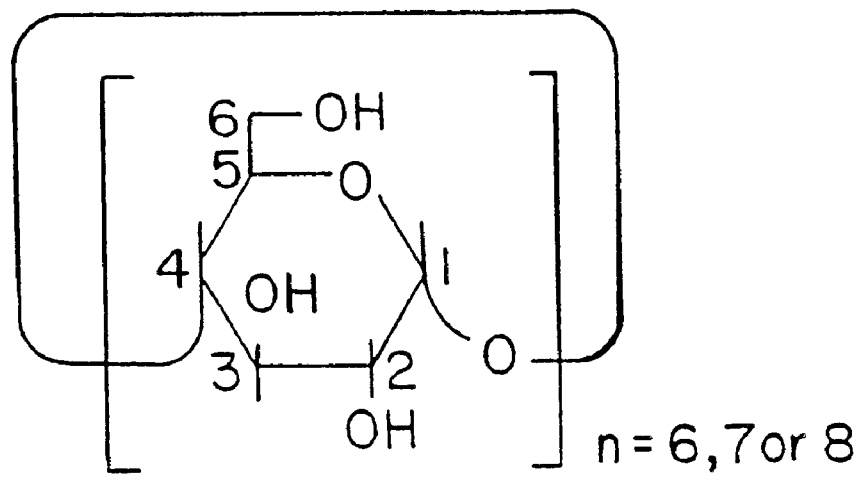
FIG. 1 (A and B) is a schematic representation of (A) the chemical structure of $\alpha$-, $\beta$- and $\gamma$-cyclodextrin monomer; and (B) of the three-dimensional shape of these cyclodextrin monomers.

The invention is directed to compounds, compositions and methods for affecting the growth of living tissue in mammals. The novel compounds of the present invention are derivatized cyclodextrin polymers having low solubility in distilled water at body temperature and a high negative charge density. The present compositions comprise a low solubility, polyanionic saccharide derivative having a relatively high density of anionic substituents and a carrier for such derivative.

One important aspect of the present compounds and compositions is the strong affinity of such materials for proteinic growth factors. Although applicants do not intend to necessarily be bound by or limited to any particular theory, it is thought that the density of the anionic groups on the saccharide compounds of the present invention is important in providing the high affinity of these compounds for tissue and growth factors. Applicants have discovered that the affinity of the present compounds and compositions for growth factors combined with the low solubility of the present saccharide derivatives provides the ability to regulate and control the concentration of growth factors in the area of a wound. In addition, the present compounds and compositions provide active agents in the form of the present derivatized saccharides which tend to adhere to living tissue. As a result, such compositions and compounds have the highly desirable ability to provide active wound healing agents at the site of an injury for extended periods of time.

The invention is also directed to methods for preparing these compositions and to methods for treating a variety of wounds resulting from accidents or surgical procedures. As the term is used herein, "wound healing" refers to the repair or reconstruction of cellular tissue. The wound may be the result of accident, such as injury or burns. The wounds treatable by the present compositions and methods also include wounds resulting from surgical procedures of any type, from minor intrusive procedures, such as catheterization or angioplasty resulting in wounding of vascular or organ surfaces, to major surgical procedures, such as bypass or organ transplant operations. Included in this concept of wound healing is the repair of injured or fragmented bone or cartilage and the promotion of the establishment of bone grafts or implants.

I. THE COMPOSITIONS

Applicants have found that compositions comprising as an active agent polyanionic saccharide derivatives having a high negative charge density and lo; solubility can be useful wound healing materials. Especially preferred are polyanionic cyclodextrin polymers.

As used herein, the term "polyanionic saccharide derivative" refers broadly to saccharide based compounds having 1.3 or more anionic substituents per sugar unit. The term sugar unit as used herein refers to an elementary monosaccharide building block which may, for example, be a hexose or pentose. Exemplary monosaccharides are glucose, fructose, amylose, etc. It is contemplated that all compounds which include a basic saccharide structure, as well as homologues, analogues and isomers of such compounds, are within the scope of the term "saccharide" as used herein. The saccharide compounds hereof may comprise, for example, disaccharides, trisaccharides, tetrasaccharides, oligosaccharides, polysaccharides and polymers of such saccharides. The term "oligosaccharide" refers to saccharides of from about 5 to about 10 sugar units having molecular weights, when unsubstituted, from about 650 to about 1300. The term "polysaccharide" refers to saccharides comprising greater than about 10 sugar units per molecule. Polysaccharides are understood to be saccharides having many sugar units possessing a variety of structures and various substituent groups. The term polymer as used herein refers to structures of repeated and similar saccharide compounds, based on monomers which are linked together to form the polymer.

Applicants have found that the relationship between the structure of the derivatized saccharide and the level of negative charge density can influence the effectiveness of the present compounds, compositions and methods. For example, the anionic substituents are preferably present in the molecule to an extent of from, on average, about 1.0 to about 4 substituents per sugar unit. Especially preferred compounds are those based on saccharides having on average at least about 1.4 anionic substituents per sugar unit. For saccharide compounds comprised of n sugar units and R substituents, it is preferred that the anionic substituents on the derivatized saccharide correspond substantially to about the following:

If n=2 to 3; average anionic R per n unit = or >3.5
n=4 to 5; average anionic R per n unit = or >2.0
n=>6; average anionic R per n unit = or >1.4.

While applicants contemplate that the anionic substituents of the present invention may be selected from a large group of known and available anionic substituents, it is generally preferred that the anionic substituents be selected from the group consisting of sulfate, carboxylate, phosphate, sulfonate, and combinations of two or more of these. Preferred compositions are based on saccharides having 6 or more sugar units and from about 2 to about 3 substituents per sugar unit, wherein the substituents comprise sulfate, sulfonate and/or phosphate substituents.

The saccharide derivatives of the present invention have a low solubility in distilled water at body temperature. As the term is used herein, "low solubility" refers to solubility of much less than about 15 grams per 100 ml of water. It refers to the ability of the present saccharide compounds to remain localized in a solid state for a substantial length of time in an aqueous medium such as physiological or distilled water. According to certain preferred embodiments, the saccharide derivatives have substantially no solubility in distilled water at body temperature. That is, it is preferred that the solubility of the saccharide derivative is much less than about 1 gram per 100 ml of distilled water, and even more preferably less than about 1 milligram per 100 ml. Such insolubility is achieved, for example, by utilizing saccharide compositions comprising polymer aggregates or dispersions of substantially solid polymer particles. While it is contemplated that various particle sizes and shapes may be utilized, it is preferred that the particles have an average particle size ranging from about a millimicron to about 1000 microns in diameter. Expressed in terns of molecular weight, the polymers comprising the polymer have, on average, a molecular weight of about one billion or greater. The high molecular weight of the preferred polymers is due to the presence of many millions of sugar units within any of the discrete undissolved entities. Alternatively, in other embodiments of the invention, particles having the desired insolubility are produced by forming a salt comprising an anionic saccharide in combination or associated with a polyvalent cationic constituent.

While the compositions of the present invention may be produced from the soluble saccharides as starting materials, as indicated above, it is also possible to employ as starting materials a sparsely soluble, quasi solid or solid saccharides, such as cellulose or starch. Utilization of these saccharide sources preferably comprises chemically or enzymatically degrading the solid saccharide, followed by providing the substituent groups in accordance with this invention.

A. Cyclodextrin Derivatives

Especially preferred according to the present invention are compositions containing a cyclodextrin derivative. Cyclodextrins are saccharide compounds containing at least six glucopyranose units forming a ring or toroid shaped molecule, which therefore has no end groups. Although cyclodextrins with up to twelve glucopyranose units are known, only the first three homologs have been studied extensively. These compounds have the simple, well-defined chemical structure shown in FIG. 1(A). The common designations of the lower molecular weight α-, β- and γ-cyclodextrins are used throughout this specification and will refer to the chemical structure shown in FIG. 1(A) wherein n=6, 7, or 8 glucopyranose units, respectively. The initial discovery of the cyclodextrins as degradation products of starch was made at about the turn of the century, and Schardinger showed that these compounds could be prepared by the action of *Bacillus macerans* amylase upon starch. In older literature, the compounds are often referred to as Schardinger dextrins. They are also sometimes called cycloamyloses.

Figure 1B:
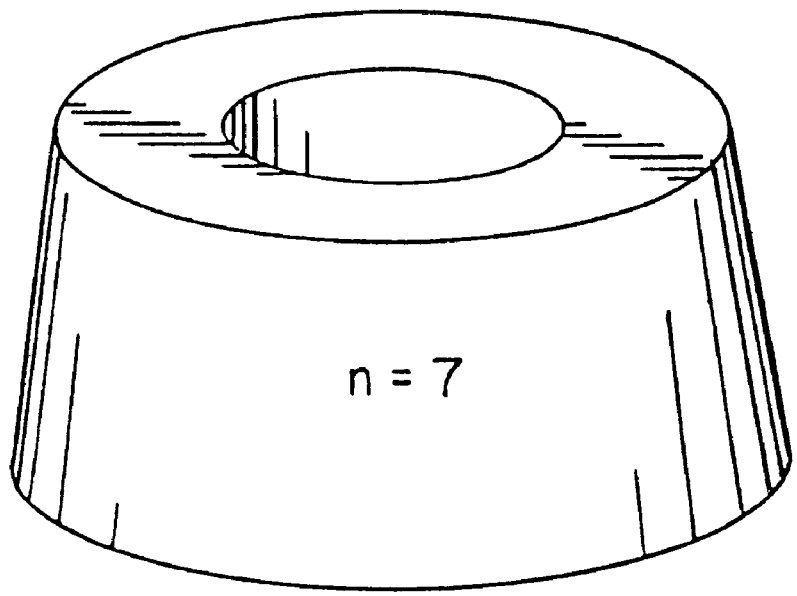

Topographically, the cyclodextrins may be represented as a torus, as shown in FIG. 1(B), the upper rim of which is lined with primary —CH$_2$OH groups, and the lower rim with secondary hydroxyl groups. Coaxially aligned with the torus is a channel-like cavity of about 5, 6 or 7.5 A.U. diameter for the α-, β-, and γ-cyclodextrins, respectively. These cavities make the cyclodextrins capable of forming inclusion compounds with hydrophobic guest molecules of suitable diameters.

The compositions of the present invention preferably include polyanionic cyclodextrin derivatives. In general, the terms "derivatized CD," "CD derivative" and the like refer to chemically modified CDs formed by reaction of the primary or secondary hydroxyl groups attached to carbons 2,3 or 6 of the CD molecule without disturbing the α (1–4) hemiacetal linkages. A review of such preparations is given in "Tetrahedron Report Number 147, *Synthesis of Chemically Modified Cyclodextrins*," A. P. Croft and R. A. Bartsch, Tetrahedron 39(9):1417–1474 (1983), incorporated herein by reference in the background (hereinafter referred to as "Tetrahedron Report No. 147").

The CD derivatives are preferably derivatized cyclodextrin monomers, dimers, trimers, polymers or mixtures of these. In general, the cyclodextrin derivatives of the present invention are comprised of or formed from derivatized cyclodextrin monomeric units consisting of at least six glucopyranose units having a (1–4) hemiacetal linkages. The preferred derivatized cyclodextrin monomers of the present invention generally have the formula (I):

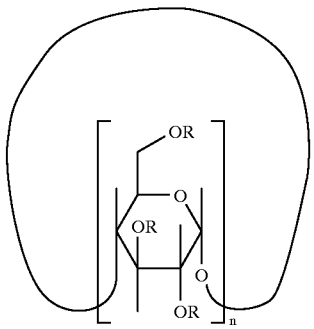

(I)

wherein at least two of said R groups per monomeric unit are anionic substituents and the remainder of said R groups, when present, are nonanionic groups selected from well known and available substituent groups. The remaining, nonanionic R groups may be, for example, H, alkyl, aryl, ester, ether, thioester, thioether and —COOH. Exemplary alkyl groups include methyl, ethyl, propyl and butyl. The remaining nonanionic R groups may be hydrophilic, hydrophobic or a combination thereof, depending upon the particular requirements of the desired composition. However, it is generally preferred that the remaining nonionic R substituents be hydrophobic in order to minimize the solubility of the compounds.

For CD monomers having the structure of Formula I wherein n is from about 6 to about 8, it is preferred that the compound have on average at least about 9 anionic R substituents per monomer unit, more preferably at least about 12 anionic R substituents per monomer, and even more preferably at least about 14 anionic R substituents per monomer. In general it is preferred that the anionic substituents be relatively evenly distributed on the monomer molecule, and accordingly compounds having the structure of Formula I wherein n is from about 6 to about 8 preferably have from about 1 to about 3 anionic R substituents per n unit, more preferably from about 1.3 to about 2.5 anionic R substituents per n unit and even more preferably from about 1.4 to about 2.2 anionic R substituents per n unit. Such structures are believed to provide the high negative charge density found to be therapeutically beneficial, with the highest charge density molecules providing excellent results.

The polyanionic cyclodextrin monomers of the type described above are important components of the preferred compositions of the present invention. The monomeric units may be present in the composition in the form of, for example, insoluble polymeric or co-polymeric structures or as insoluble precipitated salts of derivatized cyclodextrin monomer, dimer or trimer. Such salts may be formed by methods which comprise derivatizing the CD with anionic substituent and then complexing or associating the derivatized CD with an appropriate polyvalent cation to form an insoluble derivatized CD salt. In alternative and preferred embodiments, the basic monomeric structure identified above comprises the repeating unit of novel insoluble polymeric cyclodextrins, as described more fully hereinafter.

1. Cyclodextrin Polymers

According to important and preferred embodiments, the present compositions comprise derivatized cyclodextrin polymers. The present polymers have a structure corresponding to polymers formed from derivatized cyclodextrin monomers of the type illustrated above. In view of the present disclosure, it will be appreciated that polymeric materials having such structure may be formed by a variety of methods. For example, derivatized cyclodextrin polymers may be produced by polymerizing and/or cross-linking one or more derivatized cyclodextrins monomers, dimers, trimers, etc. with polymerizing agents, e.g. epichlorhydrin, diisocynanates, diepoxides and silanes using procedures known in the art to form a cyclodextrin polymer. (*Insoluble Cyclodextrin Polymer Beads, Chem.* Abstr. No. 222444m, 102:94; Zsadon and Fenyvesi, 1st. Int. Symp. on Cyclodextrins, J. Szejtli, ed., D. Reidel Publishing Co., Boston, pp. 327–336; Fenyvesi et al., 1979, Ann. Univ. Budapest, Section Chim. 15:13 22; and Wiedenhof et al., 1969, Die Starke 21: 119–123). These polymerizing agents are capable of reacting with the primary and secondary hydroxy groups on carbons 6, 2, and 3. Alternatively and preferably, the derivatized cyclodextrin polymers may be produced by first polymerizing and/or cross-linking one or more underivatized cyclodextrin monomers, dimers, trimers, etc. (eg., cyclodextrins having the structure of FIG. 1) and then derivatizing the resulting polymer with anionic substituents. Underivatized cyclodextrin polymer is available from American Maize Products Co., Hammond, Ind. in the form of an epichlorhydrin linked polymer of β-cyclodextrin. Underivatized commercially available polymers may be derivatized to produce the desired form of derivatized cyclodextrin polymer. The derivatized cyclodextrin polymers may also be formed by reacting mixtures of derivatized monomers and underivatized monomers, or by copolymerizing and/or crosslinking derivatized cyclodextrin polymers and underivatized cyclodextrin polymers. For all preparation procedures, it is preferred that the polymerization method employed result in a solid polymer product of sufficient porosity to allow diffusion penetration of molecules between the external solvent and a substantial portion of the internal anionic monomer sites.

The solubility of the present CD polymers will depend, inter alia, on the molecular weight and size of the polymer. The present derivatized CD polymers are of large molecular weight so as to remain substantially in the solid state. They are solid particulates of generally about 1 to 300 micron size.

The derivatized cyclodextrin polymer of the present invention may be available in a variety of physical forms, and all such forms are within the scope of the present invention. Suitable forms include beads, fibers, resins or films. Many such polymers have the ability to swell in water. The characteristics of the polymeric product, chemical composition, swelling and particle size distribution are controlled, at least: in part, by varying the conditions of preparation.

The cyclodextrin polymer derivative preferably comprises a polyanionic derivative of an alpha-, beta-, or gamma-cyclodextrin polymer. In preferred embodiments the anionic substituents are selected from the group consisting of sulfate, sulfonate, phosphate and combinations of two or more of the foregoing. Although it is possible that other anionic groups such as nitrate might possess some therapeutic capacity, the sulfate, sulfonate and phosphate derivatives are expected to possess the highest therapeutic potential. In preferred embodiments, at least about 10 molar percent of the anionic substituents, and even more preferably at least about 50 molar percent, are sulfate groups. Highly preferred are alpha-, beta-, and gamma-cyclodextrin polymers containing about 10–16 sulfate groups per cyclodextrin monomer, with beta-cyclodextrin tetradecasulfate polymer being especially preferred.

B. Insoluble Salt Precipitates

The present compositions may include derivatized insoluble saccharide salt precipitates, and preferably derivatized insoluble oligosaccharide salt precipitates. As the term is used herein, "salt precipitate" means a polyanionic saccharide derivative which has been associated or complexed with a suitable, non-toxic, physiologically acceptable cation to produce a salt which is substantially insoluble at body temperature. Suitable polyvalent cations which may be used to produce an insoluble salt precipitate of the present invention include Mg, Al, Ca, La, Ce, Pb, and Ba. The cations herein listed are presented generally in order of decreasing solubility, although this order may be different for saccharides of different types and degrees of anionic substitution. While all such derivatized insoluble saccharide salt precipitates are believed to be operable within the scope of the present invention, the derivatized oligosaccharides are preferred. Such oligosaccharides typically have unsubstituted molecular weights ranging from about 650 to about 1300. oligosaccharides are usually obtained by procedures of degradation of starches or cellulose which result in oligosaccharide fragments in a broad range of sizes. Cyclodextrins are generally obtained from starches in the presence of specific enzymes that favor the formation of the cyclic saccharide structures. According to certain embodiments, the cyclodextrin salt precipitates are obtained by reacting the desired cyclodextrin monomer or monomers with agents that will produce the desired anionically substituted product and subsequently exchanging the cations which were introduced by the synthesis for cations of the desired polyvalent type. This latter step will result in precipitation of the insoluble saccharide salt precipitate.

The Al, Ca and Ba salts of α-, β- and γ-CD sulfate are preferred for use in the compositions of the present invention, with Al β-CD sulfate salts being preferred in certain embodiments. As with the saccharide derivatives generally, various degrees of sulfation per glucose unit can be employed. It is generally preferred, however, that the derivatized cyclodextrin salts have an average of at least about 1.3 sulfate groups per sugar unit, and even more preferably about two sulfate groups per sugar unit. Especially preferred is β-CD-TDS which has an average of about two sulfate groups per glucose unit.

C. Polyanionic Disaccharide Derivatives

Figure 2:
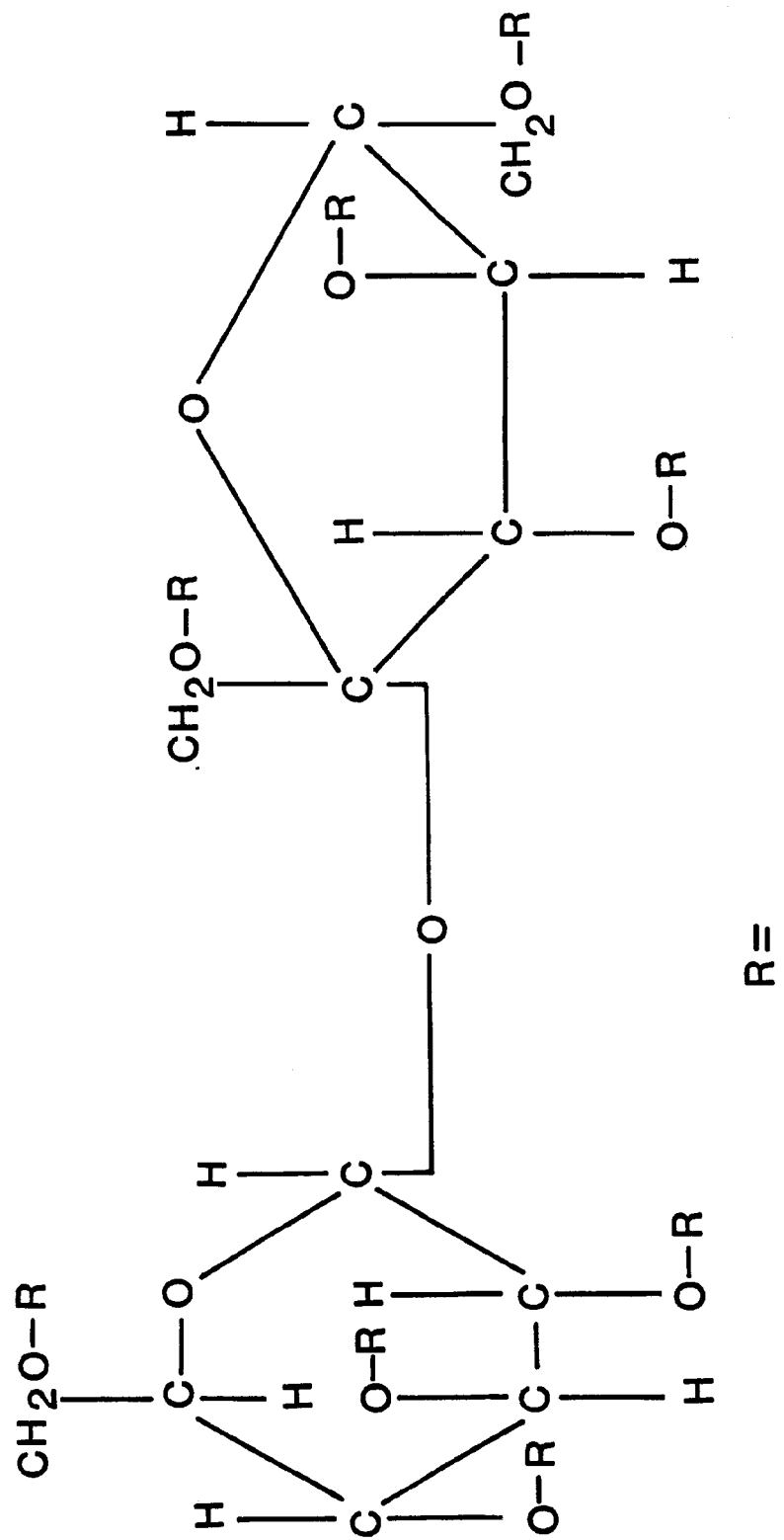
FIG. 2 is a schematic representation of the chemical structure of sucrose with the sites of anionic substituent groups indicated.

Sucralfate (Carafate®, Marian Merrill Dow, Kansas City, Mo.) is a complex salt of sucrose sulfate and aluminum hydroxide. Its structure is shown in FIG. 2. Sucralfate is an α-d-glucopyranoside, β-d-fructofuranosyl-,octakis (hydrogen sulfate) aluminum complex. Sucralfate is used to treat ulcers and was developed during studies of sulfated polysaccharides that bind pepsins but lack anti-ulcer efficacy. The sulfation of sucrose and its conjugation with a basic aluminum salt resulted in a pepsin-inhibiting molecule suitable for treatment of ulcers. Denis M. McCarthy, *Sucralfate,* 325:14 New Eng. J. Med., 1017–1025 (1991).

Applicants have found that sucralfate and other polyionic derivatives of sucrose have some properties in common with the derivatized cyclodextrins of the present invention and may provide similar solubility and affinity for growth factors. It is believed that sulfonate or phosphate derivatives of sucrose combined with polyvalent cations such as Mg, Al, Ca, La, Ce, Pb or Ba may result in compositions of low solubility which can be combined with growth factors to facilitate therapeutic delivery of these growth factors to the site of a wound. Oral administration of sucralfate has been described to have therapeutic usefulness in the treatment of stomach ulcers. According to the present invention, sucralfate and other salts of sucrose octasulfate may be used to deliver growth factor proteins to tissues or bone in need of repair, by prior complexing with growth factors, and delivering the complex physically to the site of repair.

The frequent and/or high dosage use of aluminum salts is well known to have certain health risks associated with it. Aluminum uptake is known or suspected to be associated with a number of diseases. See, for example, the extensive discussions in the books ALUMINUM AND HEALTH; A CRITICAL REVIEW (Hillel and Gitelman, Ed.), Mark Decker, Publisher, 1989 and ALUMINUM IN RENAL FAILURE, Mark E. de Broi and Jack W. Coburn, Klewer, Publisher, 1990.

Aluminum is known to produce abnormalities in bone metabolism, such as osteodystrophy, osteomalacia, impaired mineralization, etc. The introduction of aluminum into the blood stream, such as can occur in dialysis, can be particularly harmful. The following are but a few examples of reports concerning the harmful effects of aluminum: A. M. Pierides et al., Kidney Int., Vol. 18, 115–124, 1984; H. A. Ellis et al., J. Clin. Path. 32, 832, 1979. In addition to the toxic effects of Aluminum when introduced into the blood stream, oral administration of aluminum salts can also produce a variety of harmful effects including osteomalacia and osteitis; see, e.g., S. P. Andredi, J. M. Bergstein et al., N. Engl. J. Med., Vol. 310, 1079, 1984; K. A. Carmichael, M. D., Fallon et al., Am. J. of Med., Vol. 76, 1137, 1984.

Particularly prominent among aluminum's toxic effects are neural abnormalities, particularly Alzheimer's disease, in which aluminum is suspected to play an important role, although by a mechanism not yet understood. See, for example, D. R. Crapper McLachlan, B. J. Farnell, Aluminum in Neuronal Degeneration, in Metal Ions in Neurology and Psychiatry, pp. 69–87, 1985, Alan R. Liss Inc.; D. P. Pern, P. F. Good, *Uptake of Aluminum into Central Nervous*

*System Along Nasal-Olefactory Pathways*, The Lancet, May 2, P. 1028, 1987; J. D. Birchall, J. S. Chappell, *Aluminum, Chemical Physiology, and Alzheimer's Disease*, The Lancet, October, P. 1008, 1988.

Given the possible toxicity of aluminum the non-aluminum salt forms of the highly sulfated polysaccharides are preferable over the aluminum salts forms in some and perhaps all therapeutic applications. In particular, the polymeric embodiments which do not require salt precipitate formation, are particularly preferred.

Several specific embodiments of the compositions of the present invention are particularly useful for oral administration in the healing of stomach ulcers. In particular, the non-aluminum salt-containing forms of sucrose octasulfate, and most preferably the polymeric solid form of highly sulfated cyclodextrin are especially advantageous because of the absence of aluminum and its side effects.

D. The Form of the Compositions

In view of the disclosure contained herein, those skilled in the art will appreciate that the present wound healing compositions are capable of having a beneficial effect in a variety of applications. It is therefore contemplated that the compositions of this invention may take numerous and varied forms, depending upon the particular circumstance of each application. For example, the derivatized saccharide may be incorporated into a solid pill or may in the form of a liquid dispersion or suspension. In general, therefore, the compositions of the present invention preferably comprise a derivatized saccharide and a suitable, non-toxic, physiologically acceptable carrier for the saccharide. As the term is used herein, carrier refers broadly to materials which facilitate administration or use of the present compositions for wound healing. A variety of non-toxic physiologically acceptable carriers may be used in forming these compositions, and it is generally preferred that these compositions be of physiologic salinity.

For some applications involving would healing in the broadest sense, it is desirable to have available a physically applicable or implantable predetermined solid form of material containing the therapeutically active material of the invention. Accordingly, it is contemplated that the compositions of this invention may be incorporated in solid forms such as rods, needles, or sheets. They may thus be introduced at or near the sites of tissue damage or sites of implantation, or applied externally as wound dressings, etc. In such embodiments, the compositions and compounds of the present invention are preferably combined with a solid carrier which itself is bio-acceptable, or the compositions comprise suitably shaped polymer or co-polymer of the present saccharide derivatives. For many applications, it is preferred that the compositions of the present invention are prepared in the form of an aqueous dispersion, suspension or paste which can be directly applied to the site of a wound. To prepare these compositions, a polyanionic saccharide derivative, such as polyanionic cyclodextrin polymer, can be used as synthesized in solid form after suitable purification, dilution and addition of other components, if desirable, including a fluid carrier, such as saline water. This will be the case when the product, saccharide salt, saccharide polymer or the saccharide co-polymer has been synthesized such as to produce a particle form of precipitate, dispersion or suspension. After synthesis, the solid derivative may also be dried, milled, or modified to a desired particle size or solid form. The particle size can be optimized for the intended therapeutic use of the composition. In some preferred embodiments the solid particles range in size from about 1 micron to about 600 microns, with from about 200–600 microns being even more preferred. Particles ranging from about 1 to about 30 microns offer the best dispersion of growth factor and fast reactivity. For a given weight quantity of particles delivered to the biological environment, a smaller particle size assures exposure of greater particle surface area allowing greater diffusion of proteinic active ingredients into or out of the administered solid. Particles ranging from about 30 to about 100 microns offer fair dispersion of growth factors, medium reactivity and a longer period of delivery of growth factor. Particles possessing a size in excess of 100 microns will have low reactivity, but provide the longest delivery time for growth factors. In certain preferred embodiments, these large particles (>100 micron) will be used to absorb, rather than deliver growth factors in vivo.

In preferred embodiments, the carrier is an aqueous medium and the compositions are prepared in the form of an aqueous suspension of solid particulate saccharide derivative. The amount of the derivatized saccharide preferably ranges from about 1 to 30% by weight of the composition, and even more preferably from about 5 to about 15% by weight.

E. Biologically Active Protein

In certain embodiments, the compositions and compounds include and/or are combined with biologically active proteins. According to preferred embodiments, the biologically active protein exhibits a specific affinity for heparin, and, more specifically, is heparin-binding growth factor, i.e., a class of growth factors, many of which are mitogenic for endothelial cells. An example of such a growth factor is basic fibroblast growth factor. Generally it will be the heparin-binding growth factor proteins, commonly referred to as HBGF's, which may be combined with the saccharide derivatives of the present invention. Some of these are listed in Table I.

To determine whether a protein is suitable for the therapeutic compositions of the present invention, one can determine whether it has a specific affinity for heparin. A HBGF protein is one that remains substantially bound to heparin (e.g., using a derivatized column) even in the presence of an aqueous medium having a salt concentration of substantially greater than about 0.6 molar strength of NaCl. Generally, the term substantially bound refers to at least about 80% of such bound protein remaining attached under such conditions.

TABLE I

PROTEIN FACTORS

| Symbol | Name | Reference |
|--------|------|-----------|
| IL-1 | (Interleukin-1) | Henderson &. Pettipher, 1988, Biochem. Pharmacol. 37:4171; Endo et al., 1988, BBRC 136:1007, Hopkins et al., 1988, Clin. Exp. Immunol. 72:422 |
| IL-2 | (Interleukin-2) | Weil-Hillman et al., 1988, J. Biol. Response Mod. 7:424; Gemlo et al., 1988, Cancer Res. 48:5864 |
| IFNα | (Interferon α) | Pitha et al., 1988, J. Immunol. 141:3611; Mangini et al., 1988, Blood 72:1553 |
| IFNγ | (Interferon γ) | Blanchard & Djeu. 1988, J. Immunol. 141:4067; Cleveland et al., 1988, J. Immunol. 141:3823 |
| TNFα | (Tumor necrosis factor α) | Plate et al., 1988, Ann. NY Acad. Sci. 532:149; Hopkins & Meager, 1988, Clin. Exp. Immunol. 73:88; Granger et al., 1988, J. Biol. Response Med. |

TABLE I-continued

PROTEIN FACTORS

| Symbol | Name | Reference |
|---|---|---|
| EGF | (Epidermal growth factor) | 7:488 Carpenter and Cohen, 1979, A. Rev. Biochem. 48:193–216 |
| FGF | (Fibroblast growth factor, acidic and basic) | Folkman and Klagsbrun, 1987, Science 235:442–447 |
| IGF-1 | (Insulin-like growth factor-1) | Blundell and Humbel, 1980, Nature 287:781–787; Schoenle et al., 1982, Nature 296:252–255 |
| IGF-2 | (Insulin-like growth factor-2) | Blundell and Humbel |
| PDGF | (Platelet-derived growth factor) | Ross et al., 1986, Cell 46:155–169; Richardson et al., 1988, Cell 53:309–319 |
| TGF-α | Transforming growth factor- | Derynck, 1988, Cell 54:593–595 |
| TGF-β | (Transforming growth factor- | Cheifetz et al., 1987, Cell 48:409–416 |

It is known that the completing capabilities of heparin toward growth factor proteins are paralleled by its completing capabilities for certain cationic dye structures, such as azure-A, methylene blue and others. Other glycosaminoglycan saccharides are known not to function similarly. Thus such dyes have been used for many years in histology as specific stains for the presence of heparin like polysaccharides; and metachromasia, i.e. the spectral shift resulting from heparin binding on the dye has been used to identify active heparin-like compounds having the capability of modulating angiogenesis. Such dye complexing of the active protein also is similarly resistant to salt concentration as is the complexing to heparin.

In relation to this invention it has been discovered that such dye complexing, serving as a model for proteinic growth factor complexing, can usefully serve as an indicator for the desired activity of the compositions of the invention. Thus, the proteinic growth factor complexing ability of the precipitates, polymers, or co-polymers of the compositions of the present invention may be determined using dye complexing assays.

In the course of practicing heparin binding separation or chromatography for the separation of proteinic factors it has been customary and accepted that desorption of the complexed growth factor requires the added step and involvement of contacting with a very strong salt solution. The present invention makes use of the important discovery and recognition that release of protein complexed to the saccharide herein specified does not require the added step of contacting with high concentration electrolyte. While such operation would be needed for an immediate large scale desorption process as may be desired for a separation technology, the relatively very low external concentration of desorbed factor is maintained by an equilibrium process involving the complexed phase on the solid and the low biologically required solute phase in the physiological surrounding liquid. This is a basic discovery and recognition allowing the use of our compositions as delivery agents for biomedical purposes.

Generally, to prepare the growth factor containing compositions, derivatized saccharide is contacted with a solution containing a growth factor or combination of growth factors. The cyclodextrin derivative is thereafter separated from the contact fluid, resulting in an enrichment of the growth factor on the cyclodextrin derivative, and a corresponding removal of the growth factor from the fluid. The contacting solution may contain a single preseparated, preconcentrated growth factor purified from tissue or bodily fluids or growth factor obtained from recombinant DNA methods. Alternatively the contact solution may comprise viable tissue or organ materials (hereinafter organic sources) which contain a variety of growth factors. When combined with tissue or organ material containing growth factors, the saccharide derivatives of the present invention may act as extractants of these growth factors. When organic sources are used as the source for growth factors, it is preferred that the organic source used for the contacting solution have a volume greater than about 10 to about 100 times the volume of the tissue to be treated by the combined derivative and growth factor(s).

After contacting the partially or wholly completed saccharide derivative, the solid phase, can be easily separated from the fluid phase that was the source of protein to be complexed. It is preferable that the source of growth factor contains the protein as a dissolved component in the absence of solids other than the saccharides to be complexed. However, some solids in the growth factor source solution, may not necessarily be undesirable or disturbing contaminants. Separation of solids, such as tissue or organ fragments from the saccharides, may be accomplished by sedimentation, suitable filtering, centrifugation or other mechanical or other methods.

II. METHODS FOR THERAPEUTIC REGULATION OF WOUND HEALING

One aspect of the present invention relates to methods for the therapeutic regulation, and preferably in vivo regulation, of wound healing, and particularly to in vivo regulation of the concentration and diffusion of protein factors. Such methods generally comprise therapeutic biodelivery of the present compositions and compounds to the wound site. The low solubility, i.e. the solid immobilized state, of the present materials allows the compositions and compounds to be administered directly to the site of a wound and for the active ingredients to remain at the site of application for an extended period of time.

Vascular cell proliferation and abnormal accumulation of extracellular matrix in the vessel wall are common pathological features observed in arteriosclerosis, hypertension and diabetes. Such conditions are also observed following vascular injuries, such as angioplasty. Intimal hyperplasia is thought to be mediated in part by a variety of growth factors, such as platelet derived growth factor (PDGF), acting through receptors to stimulate vascular smooth muscle cell proliferation and migration from the media into the intima. Thus, applicants have discovered methods for regulating migration and proliferation of the smooth muscle cells, thereby affecting the degree of intimal thickening noted after vascular injury. The applicants have found that β-cyclodextrin tetradecasulfate can inhibit human vascular smooth muscle cell proliferation and migration in vitro when stimulated with fetal calf serum, which contains potent growth factor activity.

It is seen, therefore, that the presence or absence of growth factors at the site or vicinity of a wound has an impact upon the healing process. Applicants have found that the present compositions and compounds can be used to beneficially regulate and control biologically active proteins, such as growth factor, at the site of a wound. For example, when the present compounds and compositions are combined with growth factors prior to biodelivery as described herein, the compositions and compounds slowly release this growth factor into the immediate vicinity of the wound, thereby accelerating the wound healing process. It is contemplated that all growth factors known to accelerate or facilitate wound healing are usable in the present compositions and methods. Growth factors suitable for this acceleration of wound healing include those listed in Table I, as well as brain endothelial cell growth factor and retina-derived growth factor. As described above, heparin binding growth factors can be used to effect the repair of both soft and hard tissue. The potential uses for interferons, interleukins, and tissue growth factors are well known in the art.

The invention also relates to methods for the therapeutic administration of polyanionic saccharide derivatives, or complexes thereof, with a protein factor, wherein the saccharide derivative is combined with or comprises a portion of a biocompatible porous solid. The phrase, "biocompatible porous solid" as used herein means a solid which may be applied or administered to a mammal without provoking a substantial inflammatory response or other substantial adverse effect. Such biocompatible porous solids include membranes such as collagen-based polymeric membranes, amniotic membranes, and omentum membranes (reviewed in Cobb, 1988, Eur. J. Clin. Investig. 18:321–326). The polyanionic saccharide derivatives may be immobilized on such membranes in a preferred embodiment by contacting the derivatized saccharide with electrostatic binding partners on the membrane. Biocompatible porous solids may also include polymers of ethylene vinyl acetate, methylcellulose, silicone rubber, polyurethane rubber, polyvinyl chloride, polymethylacrylate, polyhydroxyethylacrylate, polyethylene terephthalate, polypropylene, polytetrafluoroethylene, polyethylene, polyfluoroethylene, propylene, cellulose acetate, cellulose and polyvinyl alcohol (reviewed in Hoffman, Synthetic Polymeric Biomaterials in *Polymeric Materials and Artificial Organs*, ACS Symposium Series #256, (G. Gebelein, ed.) 1988). In preferred embodiments, the cyclodextrin starting materials are co-polymerized with monomers of the biocompatible polymer material of the final product composition, so as to create a porous co-polymer. This co-polymer is subsequently reacted chemically to provide the saccharide portion with the anionic substituents required by this invention. Cyclodextrins can be coupled with reactive groups, such as amine, amide, carboxylate end groups, etc., contained in the biocompatible polymer and then subsequently derivatized with ionic substituents. More preferably the polysaccharide, such as a cyclodextrin is introduced as a co-reagent in a monomer formulation to be polymerized to a solid polymer or co-polymer, and the product is contacted subsequently with suitable agents to derivatize the saccharide component to add anionic substituents to the degree taught by this invention. Particularly advantageous for such process and products are those methods that will produce a polymer or co-polymer example of a flat polymer product of polyamide polymer, manufactured by 3M Corporation, and used as a bio-compatible patch or dressing on wounds. This biocompatible patch or dressing is designed to physically protect a wound from invasion of pathogens, and yet to have sufficient porosity to allow passage of moisture, air, etc. Applicants' invention contemplates the coupling of the active polyanionic polysaccharide with a carrier comprising such polymer, or, the coupling of the active anionic saccharide and a proteinic factor together with a polymeric carrier. Such combination is designed expressly for applications of deliberate promotion or inhibition of cellular growth processes. The HBGFs bind to the immobilized, derivatized saccharide-based molecules, either incorporated into or already present in biomembranes. Biological membranes such as omentum and amnion are well known in the art as wound dressings. Collagen based synthetic biomembranes are being used in the treatment of burns. The presence of derivatized saccharide of the present invention in natural membranes such as amnion and the ability of these derivatives to bind collagen which is used as a base for synthetic membranes will allow such biomembranes, when combined with the compositions of the present invention, to be used as novel delivery vehicles for HBGFs.

A. Restenosis

Arteriosclerosis is a disorder involving thickening and hardening of the wall portions of the larger arteries of mammals, and is largely responsible for coronary artery disease, aortic aneurisms and arterial diseases of the lower extremities. Arteriosclerosis also plays a major role in cerebral vascular disease.

Angioplasty has heretofore been a widely used method for treating arteriosclerosis. For example, percutaneous transluminal coronary angioplasty (hereinafter "PTCA") was performed over 200,000 times in the United States alone during 1988. PTCA procedures involve inserting a deflated balloon catheter through the skin and into the vessel or artery containing the stenosis. The catheter is then passed through the lumen of the vessel until it reaches the stenotic region, which is characterized by a build up of fatty streaks, fibrous plaques and complicated lesions on the vessel wall, which result in a narrowing of the vessel and blood flow restriction. In order to overcome the harmful narrowing of the artery caused by the arteriosclerotic condition, the balloon is inflated, thus flattening the plaque against the arterial wall and otherwise expanding the arterial lumen.

Although PTCA has produced excellent results and low complication rates, there has, however, been difficulties associated with the use of this technique. In particular, the arterial wall being enlarged frequently experiences damage and injury during expansion of the balloon against the arterial wall. While this damage itself is not believed to be particularly harmful to the health or the life of the patient, the healing response triggered by this damage can cause a reoccurrence of the arteriosclerotic condition. In particular, it has been observed that the smooth muscle cells associated with the stenotic region of the artery initiate cell division in response to direct or inflammatory injury of the artery. As the smooth muscle cells proliferate and migrate into the internal layer of the artery, they cause thickening of the arterial wall. Initially, this thickening is due to the increased number of smooth muscle cells. Subsequently, however, further thickening of the arterial wall and narrowing of the lumen is due to increased smooth muscle cell volume and accumulation of extracellular matrix and connective tissue. This thickening of the cell wall and narrowing of the lumen following treatment of arteriosclerosis is referred to herein as restenosis.

Although applicants do not wish to be bound by any theory or theories for the basis of restenosis, it is believed that restenosis is due in part to the presence of growth factors produced by injured endothelium which activate excessive proliferation of the smooth muscle cells which are exposed to the endothelial injury. Accordingly, applicants have found that the present saccharide derivatives, when substantially free of growth factors prior to biodelivery, are extremely effective for preventing or at least substantially reducing intimal thickening following balloon angioplasty. By virtue of their affinity for growth factors, such compositions can provide an in vivo absorption or reduction of the local concentration and/or diffusion of such growth factors. That is, such wound site growth factors, whether they are produced by the cells at the wound site or are otherwise in the bloodstream, can be taken up by the present saccharide derivatives, thereby reducing the restenoic effect of such materials on the wounded tissue.

According to the present methods, mammals, including humans, which have arterial regions subject to angioplasty, are treated by administering to the mammal a polyanionic saccharide derivative of the present invention in an amount effective to inhibit arterial smooth muscle cell proliferation. It is contemplated that the degree of restenosis inhibition may vary within the scope hereof, depending upon such factors as the patient being treated and the extent of arterial injury during angioplasty. It is generally preferred, however, that the saccharide derivative be administered in an amount effective to cause a substantial reduction in restenosis. As the term is used herein, substantial reduction in restenosis means a post treatment restenosis value of no greater than about 50%. According to preferred embodiments, the post treatment restenosis value is no greater than about 25%. As the term is used herein, post-treatment restenosis value refers to the restenosis value measured at about one month after angioplasty The term restenosis value refers to the restenosis rate calculated as a loss of greater than or equal to 50% of the initial gain in minimum lumen diameter achieved by angioplasty.

Thus, the present invention contemplates a method of inhibiting restenosis in a patient which comprises administering to the patient an amount-of a saccharide-based derivative effective to inhibit formation of a restenotic lesion in a patient who has undergone angioplasty. It is contemplated that the saccharide derivative may be administered before, during and/or after angioplasty treatment of the stenosed artery. It is generally preferred that the administration comprise administering the compound locally at the wound site. In preferred embodiments, local administration comprises infusing the saccharide derivative directly into the injured tissue. In the case of restenosis, such step preferably comprises infusing the compound directly into the arterial wall at the site of the angioplasty.

Applicants have surprisingly found that particularly beneficial antirestenoic results are obtained for embodiments in which the step of administering the saccharide derivative also comprises the step of dilating the vessel lumen to effect angioplasty. For example, applicants have found that a preferred administration step comprises infusing an aqueous suspension or dispersion of saccharide derivative directly into the arterial wall at the site of balloon angioplasty. This is preferably accomplished using a modified infusion balloon catheter having a plurality of holes in the wall of the balloon portion of the catheter. These holes are configured and sized to allow the balloon to be both inflated and to leak the inflation solution through the wall of the balloon. According to preferred embodiments, the balloon is inflated under relatively low pressure conditions, such as 2–3 atmospheres. Examples of porous balloon catheters which may be used to apply the compositions of the present invention are made by U.S.C.I.- Bard and Schneider. Balloons of this type are referred to as Wolinsky balloons or "sweating balloons." It is anticipated that a variety of infusion angioplasty balloon catheters may be used for application of the compositions of the present invention and that one skilled in the art would be readily able to determine which types of balloon infusion catheters would be appropriate. Another technique which involves the local administration of the saccharide derivatives of the present invention utilizes bioabsorbable intravascular stents. The saccharides of the present invention, particularly the cyclodextrin polymer derivatives may be incorporated into a bioabsorable stent and that stent positioned at or near the site of tissue damage.

It will be appreciated by those skilled in the art that the particular characteristics and properties of the suspension containing the saccharide derivative may vary widely depending upon numerous factors not necessarily related to the present invention. However, the administration step preferably comprises infusing an aqueous suspension or dispersion of polyanionic saccharide derivate particles, and preferably a suspension of sulfated beta-cyclodextrin polymer particles, ranging in size from about 1 to 600 microns directly into the arterial wall at the site of balloon angioplasty. Applicants believe that such particles instilled into the arterial wall will remain present at the site of application for several days, in sufficient quantity to result in an inhibition of restenosis.

The aqueous suspension comprises a aqueous carrier of physiological salinity and an active saccharide derivative. The active saccharide derivative is preferably present in an amount: ranging from about 1 to about 30% by weight, and even more preferably from about 5 to about 15% by weight of the composition. In preferred embodiments, derivatized saccharides, and preferably cyclodextrin sulfate polymer particles, are applied at about the time of angioplasty.

In some instances it may be desirable to prevent restenosis but allow angiogenesis. To meet these requirements it is preferred to use a dispersion of an Al or Ba salt of a polyanionic saccharide derivative, and even more preferably an Al or Ba salt of a poly sulfated beta-cyclodextrin. If it is desired to allow the normal progression of angiogenesis at the vascular injury site while simultaneously inhibiting restenosis, it is preferred to use sucralfate, an aluminum salt of sucrose octasulfate available from the Marian Merrill Dow Company, Kansas City, Mo.

B. Inhibition of Intimal Thickening of Vein Grafts

Venous segments are frequently harvested at the time of surgery and used as bypass grafts to treat vascular occlusive disorders. Specifically, they have been used in the coronary, renal, femoral and popliteal arterial circulations, by way of example. One major limitation of this form of therapy is that intimal thickening occurs which compromises the luminal cross-sectional area and results in reduced flow. This frequently, but not exclusively occurs at the anastoinosis. Applicants propose that the placement of β-cyclodextrin tetradecasulfate polymeric particles in the perivascular space at the time of surgery, will substantially limit the ingrowth of smooth muscle cells into the intima and will improve the long term success of these grafts.

C. Angiogenesis

Angiogenesis is the formation of new blood vessels. Angiogenic stimuli cause the elongation and proliferation of endothelial cells and the generation of new blood vessels. A number of the HBGFs are known to promote angiogenesis. The new blood vessels produced by angiogenesis result in neovascularization of tissue.

There are a Variety of diseases associated with deficient blood supply to tissue and organs. A deficiency of this kind, known as ischaemia, may be due to the functional constriction or actual obstruction of a blood vessel. These diseases can be grouped into cardiac, cerebral and peripheral ischemic diseases. Cardiac ischaemia may result in chronic angina or acute myocardial infarction. Cerebral ischaemia may result in a stroke. Peripheral ischaemia may result in a number of diseases including arterial embolism and frostbite. In severe cases of peripheral ischaemia, necrosis of the tissues supplied by the occluded blood vessels necessitates amputation. To overcome ischaemia, an alternative blood supply to the affected tissue must be established.

According to preferred embodiments, angiogenesis is promoted by first contacting a saccharide derivative of the present invention with growth factor(s) and then administering the composition locally to the location of the ischemic tissue, by hypodermic injection for example, to promote angiogenesis and the formation of collateral blood vessels. As the term is used herein, collateral blood vessels are blood vessels which are absent under normal physiological conditions but develop in response to appropriate stimuli, such as the presence of HBGFs. It is anticipated that administration of compositions which include saccharide derivative and growth factor will result in the formation of collateral blood vessels and revascularization of ischemic tissue.

In preferred embodiments, angiogenesis is promoted by methods in which the saccharide derivative comprises a highly anionic cyclodextrin derivative or a salt form of same, and even more preferably a polysulfated polymer or copolymer of a cyclodextrin. It is preferred that the cyclodextrin derivative be combined with basic fibroblast growth factor at a cyclodextrin:basic fibroblast growth factor weight ratio of from about 10:1 to 100:1.

D. Tissue and Organ Grafts or Transplants

As described above, HBGFs are known to stimulate neovascularization and endothelial cell growth. In transplantation, the graft represents a wound, and success of the grafting procedure depends critically on the rapidity of establishing an adequate blood supply to the grafted or transplanted tissue. Thus, we envision the application of the compositions of the present invention combined with growth factor(s) at the site of the graft to promote the establishment of an adequate blood supply to the grafted or transplanted tissue. The growth factor-containing compositions may be coated on the surfaces to be joined, sprayed on the surfaces, or applied in the form of an aqueous suspension with or without viscosity enhancers such as glycerol. In addition, the organ or tissue to be grafted or transplanted may be presoaked in a treating solution containing the compositions of the present invention, prior to transplantation. The compositions of the present invention may also be injected into the transplant site or surface of both items to be joined.

In a preferred method for preparing the compositions used in treating grafted or transplanted tissue and organs, the saccharide derivatives of the present invention are precontacted with growth factor containing organic sources (e.g., tissue or organ debris, ground matter, or liquid extract) so as to extract the growth factors present in these sources. In highly preferred methods, the organic source used for contact is about 10 to about 100 times greater in volume than the transplanted or grafted tissue to be treated by the composition. A more direct and often more economic method will involve contacting the saccharide derivatives of the present invention with growth factor substances created by recombinant biochemical and biotechnological procedures. In this manner specific growth factor proteins are more readily chosen for a contemplated therapeutic application.

E. Bone Grafting and Transplantation

The response of bone to injuries such as fractures, infection and interruption of blood supply is relatively limited. In order for the damaged bone tissue to heal, dead bone must be resorbed and new bone must be formed, a process carried out in association with new blood vessels growing into the involved area. HBGFs can induce neovascularization and the proliferation of bone forming cells. It is therefore contemplated to use the present compounds in combination with growth factor for the purposes of aiding the healing of bone fractures, the joining of implanted and host bone, and the mineralization of bone (where such is intended).

In preferred embodiments, the present saccharide derivatives are combined with growth factors and powdered bone substance and/or finely dispersed demineralized bone matter to form a paste. Suitable methods for preparation of such a paste are presented in *Repair of Major Cranio-Orbital Defects with an Elastomer Coated Mesh and Autogenous Bone Paste*, Mutaz B. Habal et al., 61:3, Plastic and Reconstructive Surgery, 394, 396 (1978). The bone tissue used to produce the paste may be obtained from iliac crest or calvarium. It is preferred to use autogenous bone for implant purposes and to use partially demineralized bone over fully demineralized bone powder. Demineralized bone powder obtained from allogenic and xenogeneic sources may be used in preparing the bone powder. To make a soft paste absorbable cellulose cotton or similar material may be used. Although applicants do not wish to be bound by any theory or theories, it is thought that the bone paste produced by these methods functions as an induction matrix from which new bone will form after being invaded with a network of blood vessels. The paste is applied to the surfaces of bone to be joined in implant procedures or used to fill fractures of contour bone to be repaired.

F. Skin Ulcer Healing

One debilitating disorder affecting millions of people including, but limited to the aged, paraplegics, trauma victims, and diabetics are cutaneous nonhealing skin ulcers or decubiti. In many cases, inadequate blood supply to the damaged tissue prevents the delivery of adequate nutrients for healing. It is anticipated that the application of polymeric beads of cyclodextrin derivatives, preabsorbed with combinations of compounds such as epidermal growth factor and basic fibroblast growth factor, to the ulcer directly, will lead to increased angiogenesis, improved blood supply, increased keratinocyte ingrowth, and faster ulcer closure and healing.

G. Dermatological Applications

The control of blood vessel growth is an important aspect of normal and of pathological states encountered in dermatology. In particular, the abnormal growth of cellular materials and vessels accompanies several pathological states, psoriasis being one prominent example. In many cases excesses of growth stimulating protein factors are involved. Abnormalities of this type are often associated with imbalances in proteinic growth factors.

For example, in the case of patients with cutaneous mastocytosis, extracts from involved skin had 15-fold higher levels of chymotryptic activity than extracts of uninvolved skin or from control samples of patients without such deficiency. (See *Human Skin Chymotryptic Protease*, N. M. Schechter, J. E. Fraki, J. C Geesin, G. S. Lazarus, J. Biol. Chem., 258, 2973–2978, 1903. The Chymase Involved Is a Heparin Binding Factor (See S. Sayama, R. V. Iozzo, G. S. Lazarus, N. M. Schechter, *Human Skin Chymotrypsin-like Proteinase Chymase*, J. Biol. Chem. 262, 6800–6815, 1987. It appears that the chymotrypsin like proteases can degrade the epidermal junction and can result in epidermal-dermal separation (See Sayama et al. above).

Another example of a growth promoting factor involved in dermal abnormalcies is epidermal plasminogen activator, which is elevated in a variety of dermal pathologies (See *Epidermal Plasminogen Activator is Abnormal in Cutaneous Lesions'*, P. J. Jensen et al., J. Invest. Dermat. 90–777–782, 1988).

Certain embodiments of this invention, namely highly sulfated solid dispersions or other physical variants of highly sulfated polysaccharides, and preferably those comprising cyclodextrin structures, are particularly amenable to dermal therapy in those cases where excess growth of cellular components is involved. In such case the agents of the present invention can be introduced at or near the tissue involved. This may be accomplished by cutaneous or subcutaneous injection of fine particle dispersion of the agent, or the implantation of solid polymer shapes suitably shaped for effective contact, or the agent may be comprised in material such as patches, or other suitable forms of externally applied materials containing agents of the invention.

It will be understood that depending on the pathology and disease condition, the application of the agents of this invention without pre-contacting with proteinic growth factor is contemplated. This will be the case in conditions as exemplified above, where it is intended to reduce any growth promoting factor or factors.

In other cases of dermal damage or disease, and in certain phases of treatment, it may be desirable to use the combined proteinic factors. This would be the case in connection with healing processes where angiogenesis, that is the establishment of new and added blood supplies are desired.

EXAMPLES

The following examples are provided to illustrate this invention. However, they are not to be construed as necessarily limiting the scope of the invention, which scope is determined by the appended claims. All amounts and proportions shown are by weight unless explicitly stated to be otherwise.

Example 1

PREPARATION OF SULFATED BETA-CYCLODEXTRIN POLYMER

Beta-cyclodextrin polymer beads (American Maize Products) of 20–60 mesh particle size were derivatized to form a novel immobilized CD polymer sulfate derivative according to the present invention. The composition approaches a degree of sulfation of nearly two sulfates per glucose ring of the CD polymer. About 0.4 g of carefully dried polymer were reacted with about 1.7 g of 6 trimethylammonium sulfur trioxide complex (Aldrich) in about 100 ml of dried dimethylformamide (DMF), with mild agitation at about 62 to 72° C. for 3 to 4 days. The solids were washed in DMF, reacted with 30% aqueous sodium acetate for 24 hours, and washed and stored in distilled water. The sulfur content of the product was about 114.7 wt. %. This compares favorably to the value of 17.5% if the polymer mass were composed 100% of β-cyclodextrin tetradecasulfate without cross-linking components, and all glucose hydroxyl units were sterically available (which cannot be expected for the polymer).

Example 2

PREPARATION OF DERIVATIVES OF CYCLODEXTRIN (A) β CD-TDS(Na):

β-cyclodextrin (99% pure dihydrate) was purchased from Chemalog (a division of General Dynamics Corp.), South Plainfield, N.J.

About 5.0 grams of β-cyclodextrin (about 4.4 mmoles, i.e., about 92 meq) —OH) was dissolved in about 250 ml of dimethyl-formamide (DMF). To this solution was added about 15 grams of $(CH_3)_3N-SO_3$ (about 108 mmoles) in a single portion and the reaction mixture was heated to about 70° C. After two hours at about 70° C., a gummy material began to precipitate. The reaction mixture was maintained at 70° C. with vigorous stirring, and then cooled to room temperature. The DMF layer was then decanted and discarded, and the solid residue was dissolved in about 250 ml of water followed by addition of about 75 ml of 30% sodium acetate. The mixture was stirred vigorously for 4 hours and then poured into about 4000 ml of ethanol. After standing overnight, the mixture was filtered to recover the crystallized solids. The filter cake was washed with ethanol (absolute) followed by diethyl ether. The product was then dried under vacuum over $P_2O_5$. About 10.3 grams of white powder was recovered. The product was hygroscopic.

The product was analyzed under conditions such that sorption of water was minimized. Elemental analysis gave the following results: C=18.84, H=2.65, S=17.33 (Calculated for $C_6H_8O_{11}S_2Na_2$; C=19.67, H=2.19, S=17.49) . $[\alpha]D^{22}$=75° (C=2.63 in 0.5M NaCl). The analysis corresponds to that expected for an average substitution of two hydroxyl groups for each glucopyranose unit, i.e. 14 hydroxyls per CD molecules. The calculated yield for such β-CD-TDS salt is 10.96 grams, about 6% higher than the observed 10.3 grams.

(B) α- and γ-CD-S (Na salt):

The procedure described above was used for these preparations except that about 86 mmoles of $CH_3N-SO_3$ was used with β-CD, and about 117 mmoles with the γ-CD.

The sulfated α-CD salt analyzed C=18.76; H=2.60; S=16.22. This corresponds on average to a substitution of about 11.7 hydroxyl units per β-CD molecule.

The sulfated γ-CD salt analyzed C=18.92; H=2.69; S=14.84. This corresponds on average to a substitution of about 14 hydroxyl groups per γ-CD molecule.

(C) β 3 $CD-SO_4$ (Na salt) (7.1 wt %) S):

About 1.0 gm of β-cyclodextrin was dissolved into about 50 ml of DMF. To this solution was added about 883 mg of $(CH_3N\ SO_3$(7.2 equivalents). The solution was held at about 75° C. for about 12 hours, at which time no precipitate had formed. The reaction mixture was cooled to room temperature. To the solution was added about 200 ml of ethanol. The resulting colloidal solution was then poured into about 600 ml of diethyl ether. A white solid formed in 2 hours. The solid was collected by filtration and then was dissolved in about 30 ml $H_2O$. This solution was stirred for 2 hours. After stirring, the solution was poured into about 900 ml of 2:1 EtOH-$Et_2O$ solution. Crystals formed over an 8 hour period. The crystals were collected and washed with $Et_2O$. The product was dried over $P_2O_5$ under vacuum. About 1.18 gm of powder was recovered. (72.4% yield).

Elemental analysis of the product showed C=32.49; H=4.99; and S=7.06. This corresponds on average to a substitution of about 3.5 hydroxyls per β-CD molecule.

(D) β-CD-Propoxylate~14 $SO_4$

β-CD-(hydroxy-n-propyl ether) was obtained from American Maize-Products Co. (Hammond, Ind.) and the procedure described above was used to prepare the sulfate salt, β-CD-(~4Pr~14 $SO_4$)

Example 3

PREPARATION OF GROWTH FACTORS

Human recombinant basic fibroblast growth factor (bFGF) was provided by Takeda Chemical Industries, Ltd. It was purified from *E. coli* as previously described (Kurokawa et al., 1987, FEBS. Letters 213:189–194 and Iwane et al., 1987, Biochem. Biophys. Res. Commun. 146:470–477).

Rat chondrosarcoma-derived growth factor (ChDGF) was isolated from the transplantable tumor as previously described (Shing et al., 1984, Science 223:1296–1298). About one hundred ml of the crude extract prepared by collagenase digestion of the tumor was diluted (1:1) with about 0.6M NaCl in about 10 mM Tris, pH 7 and loaded directed onto a heparin-Sepharose® column (1.5×9 cm) pre-equilibrated with the same buffer. The column was rinsed with about 100 ml of about 0.6M NaCl in about 10 mM Tris, pH 7. ChDGF was subsequently eluted with about 18 ml of about 2M NaCl in about 10 mM Tris, pH7.

Example 4

BETA-CYCLODEXTRIN AFFINITY CHROMATOGRAPHY OF FGF

The insoluble sulfated beta-cyclodextrin polymer (about 0.5 ml bed volume), was incubated with about 0.5 ml of about 0.1M NaCl, about 10 mM Tris, about pH 7 containing about 1,000 units of human recombinant bFGF at about 4° C. for about 1 hour with mixing. Subsequently, the polymer was rinsed stepwise with about 2 ml each of about 0.1, 0.6, and 2M NaCl in about 10 mM Tris, pH 7. All fractions eluted from the polymer were assayed for growth factor activity.

Example 5

GROWTH FACTOR ASSAY

Growth factor activity was assessed by measuring the incorporation of [$^3$H]thymidine into the DNA of quiescent, confluent monolayers of BALB/c mouse 3T3 cells in 96-well plates. One unit of activity was defined as the amount of growth factor required to stimulate half-maximal DNA synthesis in 3T3 cells (about 10,000 cells/0.25 ml of growth medium/well). For determination of specific activities, protein concentrations of the crude extract and the active fraction eluted from heparin-Sepharose column were determined by the method of Lowry et al. (1952, J. Biol. Chem. 193:265–275). Protein concentrations of the pure growth factor were estimated by comparing the intensities of silver-stained polypeptide bands of SDS-polyacrylamide gel to those of the molecular weight markers.

Example 6

AFFINITY OF FIBROBLAST GROWTH FACTOR FOR BETA-CYCLODEXTRIN TETRADECASULFATE POLYMER

Figure 3:
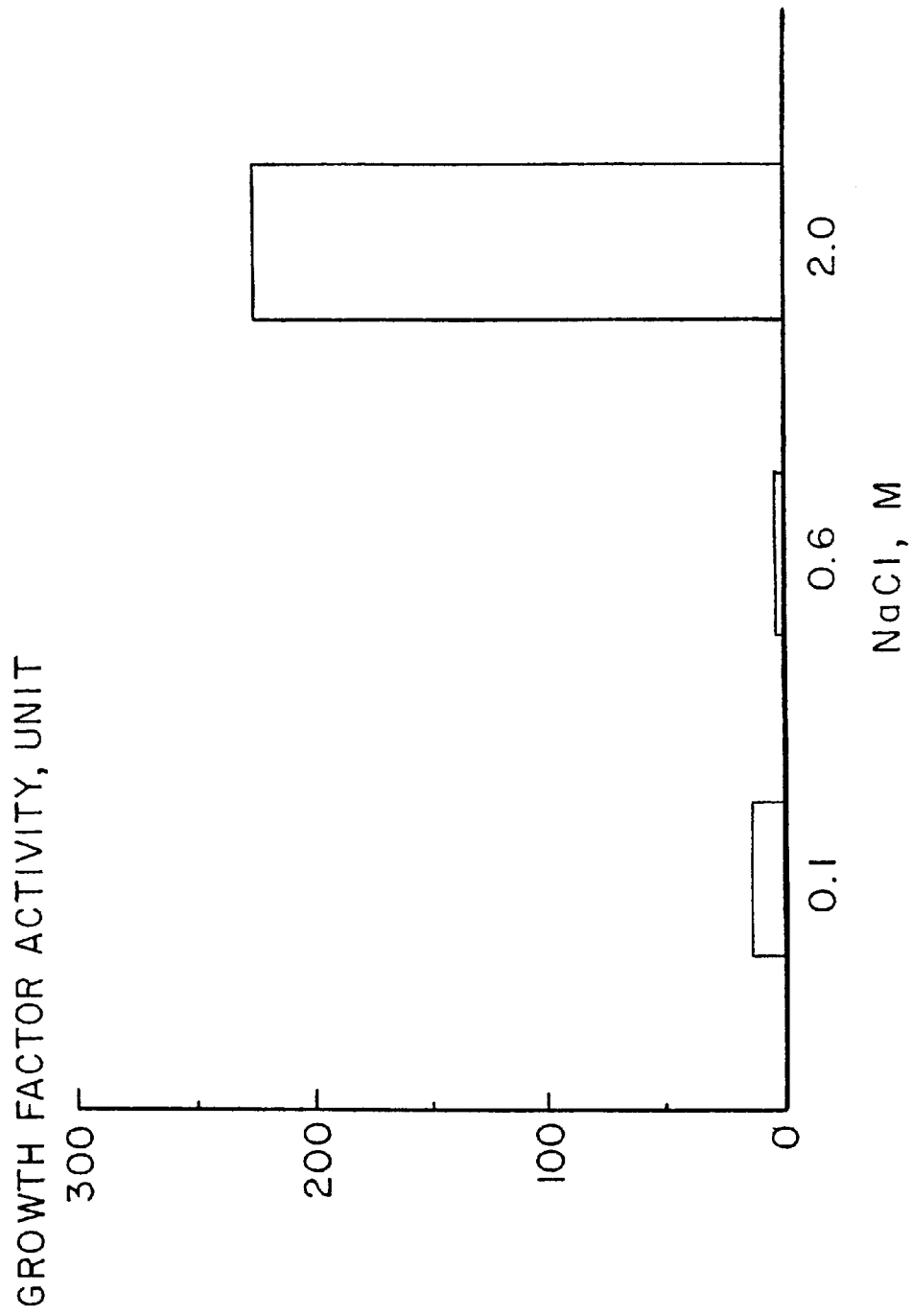
FIG. 3 shows the affinity of beta-cyclodextrin tetradecasulfate polymer for basic fibroblast growth factor.

Human recombinant bFGF (about 1000 units) was incubated with sulfated beta-cyclodextrin polymer. The polymer was subsequently eluted stepwise with about 0.1M, 0.6M, and 2M NaCl. The results are shown in FIG. 3.

While most of the growth factor activity remained bound to the polymer at about 0.6M NaCl, about 230 units of three activity was recovered when eluted with about 2M NaCl. These results indicate that basic fibroblast growth factor has a very strong affinity for beta-cyclodextrin tetradecasulfate and is at least comparable to that of FGF for heparin. The activity peak was analyzed by SDS polyacrylamide gel electrophoresis followed by a silver stain. Lane 2 in FIG. 4 shows the polypeptide band of basic fibroblast growth factor.

Figure 5:
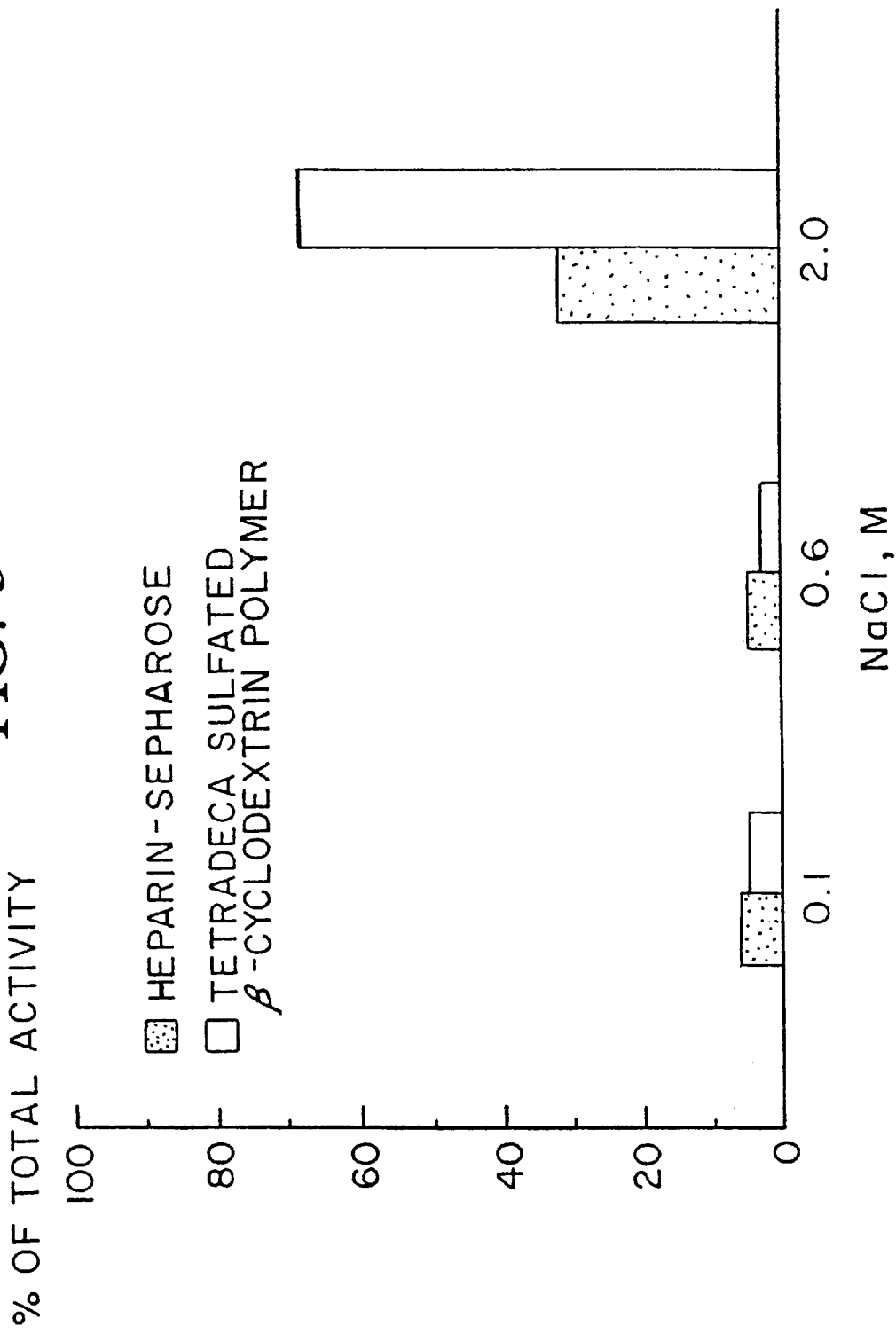
FIG. 5 compares the affinities of heparin and beta-cyclodextrin tetradecasulfate polymer for chondrosarcoma derived growth factor.

The affinities of heparin and beta-cyclodextrin tetradecasulfate for chondrosarcoma derived growth factor were also tested. Chondrosarcoma extracts which contained about 500 units of growth factor activity were incubated individually with heparin-Sepharose® and beta-cyclodextrin tetradecasulfate polymer. The beads were subsequently eluted stepwise with about 0.1M, 0.6M, and about 2M NaCl. The results are shown in FIG. 5. Approximately 32% and 68% of the total activity was; recovered at 2M NaCl with heparin Sepharoses and beta-cyclodextrin tetradecasulfate polymer, respectively.

What is claimed is:

1. A composition for modulating growth of a tissue of a mammal, the composition comprising a growth-modulating polyanionic cyclodextrin derivative monomer, wherein said monomer comprises at least six glucopyranose units and at least two, but fewer than ten, anionic substituents, wherein the solubility of said monomer in distilled water at body temperature is less than about 15 grams per 100 milliliters, and further wherein said monomer is not incorporated into a polymer or bound to a solid surface.

2. The composition of claim 1, wherein the solubility of said monomer in distilled water at body temperature is less than about 1 gram per 100 milliliters.

3. The composition of claim 1, wherein the solubility of said monomer in distilled water at body temperature is less than about 100 milligrams per 100 milliliters.

4. The composition of claim 1, wherein said monomer is substantially insoluble in distilled water at body temperature.

5. The composition of claim 1, wherein said monomer is selected from the group consisting of alpha-, beta-, and gamma-cyclodextrin.

6. The composition of claim 1, wherein each of said glucopyranose units has an average of about 1.0 to about 1.4 anionic substituents.

7. The composition of claim 1, wherein said monomer has more than about six anionic substituents.

8. The composition of claim 1, wherein said monomer has fewer than about six anionic substituents.

9. The composition of claim 1, wherein at least one of said anionic substituents is selected from the group consisting of sulfate, carboxylate, phosphate, and sulfonate.

10. The composition of claim 1, wherein said monomer comprises a hydrophobic substituent.

11. The composition of claim 10, wherein said hydrophobic substituent is selected from the group consisting of alkyl, aryl, ester, ether, thioester, thioether, methyl, ethyl, propyl, and butyl.

12. The composition of claim 3, further comprising a physiologically acceptable cation.

13. The composition of claim 12, wherein said monomer is substantially insoluble in distilled water at body temperature.

14. The composition of claim 12, wherein said cation is a polyvalent cation.

15. The composition of claim 14, wherein said polyvalent cation is a polyvalent cation of an atom selected from the group consisting of Mg, Al, Ca, La, Ce, Pb, and Ba.

16. The composition of claim 12, wherein said cation is trivalent.

17. The composition of claim 16, wherein said trivalent cation is a trivalent cation of an atom selected from the group consisting of Al, La, and Ce.

18. The composition of claim 1, further comprising a protein which exhibits a specific affinity for heparin.

19. The composition of claim 18, wherein said protein is a heparin binding growth factor.

20. The composition of claim 19, wherein said heparin binding growth factor is selected from the group consisting of brain endothelial cell growth factor, retina-derived growth factor, interleukin-1, interleukin-2, interferon alpha, interferon gamma, tumor necrosis factor alpha, epidermal growth factor, acidic fibroblast growth factor, basic fibroblast growth factor, insulin-like growth factor-1, insulin-like growth factor-2, platelet-derived growth factor, transforming growth factor-alpha, and transforming growth factor-beta.

21. The composition of claim 1, further comprising a physiologically acceptable carrier.

22. The composition of claim 21, wherein said carrier is a fluid carrier, and wherein said composition is in a form selected from the group consisting of a dispersion, a suspension, and a paste.

23. The composition of claim 21, wherein said composition is a solid.

24. The composition of claim 18, further comprising a physiologically acceptable carrier.

25. A method of extracting a growth factor from a medium comprising a growth factor, the method comprising the steps of
contacting said medium with a composition comprising a growth-modulating polyanionic cyclodextrin derivative monomer under conditions which permit binding of said growth factor to said composition, wherein said monomer comprises at least six glucopyranose units and at least two, but fewer than ten anionic substituents, wherein the solubility of said monomer in distilled water at body temperature is less than about 15 grams per 100 milliliters, and wherein said monomer is not incorporated into a polymer or bound to a solid surface; and separating said composition having said growth factor bound thereto from said medium.

26. The method of claim 25, wherein said medium is a fluid.

27. The method of claim 26, wherein said fluid is a bodily fluid of a mammal.

28. The method of claim 25, wherein said medium is a tissue of a mammal.

29. The composition of claim 14, wherein said composition forms a precipitate in aqueous solution.

* * * * *